United States Patent
Wurster et al.

[11] Patent Number: 5,556,407
[45] Date of Patent: Sep. 17, 1996

[54] ANVIL SHEARS FOR SURGICAL PURPOSES

[76] Inventors: Helmut Wurster, Mozartstrasse 20, D-7519 Oberderdingen; Karl Von Rauch, Lindenstr. 13, 2217 Kellinghusen, both of Germany

[21] Appl. No.: 17,268

[22] Filed: Feb. 12, 1993

[30] Foreign Application Priority Data

Feb. 12, 1992 [DE] Germany .................. 42 04 051.5

[51] Int. Cl.⁶ .................................. A61B 17/00
[52] U.S. Cl. ................................. 606/174; 30/134
[58] Field of Search ....................... 606/167, 170, 606/174, 205–209; 128/751; 30/251

[56] References Cited

U.S. PATENT DOCUMENTS

| | | | |
|---|---|---|---|
| 2,518,994 | 8/1950 | Miller | 606/205 |
| 4,662,371 | 5/1987 | Whipple et al. | 606/174 |
| 4,887,612 | 12/1989 | Esser et al. | 606/174 |
| 4,944,093 | 7/1990 | Falk | 606/174 |
| 5,009,661 | 4/1991 | Michelson | 606/170 |
| 5,152,780 | 10/1992 | Howkanen et al. | 606/205 |
| 5,170,800 | 12/1992 | Smith et al. | 606/170 |
| 5,171,256 | 12/1992 | Smith et al. | 606/170 |
| 5,176,695 | 1/1993 | Dulebohn | 606/170 |
| 5,196,023 | 3/1993 | Martin | 606/167 |
| 5,217,460 | 6/1993 | Knoepfler | 606/208 |

FOREIGN PATENT DOCUMENTS

| | | | |
|---|---|---|---|
| 245402 | 4/1912 | Germany | 606/174 |
| 2904115 | 8/1980 | Germany | 606/174 |
| 8900376 | 4/1989 | Germany . | |
| 9109097 | 10/1991 | Germany . | |

*Primary Examiner*—Michael Powell Buiz
*Assistant Examiner*—Nancy Mulcare
*Attorney, Agent, or Firm*—Evenson McKeown Edwards & Lenahan, PLLC

[57] ABSTRACT

The invention relates to anvil shears for surgical purposes, particularly for laparoscopic operations. The shears have an anvil (10) and a blade (40) pivotably fitted thereto, which is closed against the anvil by means of an operating rod (30) displaceable in the longitudinal direction of the shears. For improving the cutting action, according to the invention the blade (40) is displaceably mounted on the anvil in its longitudinal direction (41) and is subject to the action of a force forcing the blade into the distal advanced position. The force exerted for closing the blade (40) with the operating rod (30) is opposed by the pretensioning force (54), so that on encountering a material to be cut a cutting movement is performed in the longitudinal direction (41) of the blade.

10 Claims, 1 Drawing Sheet

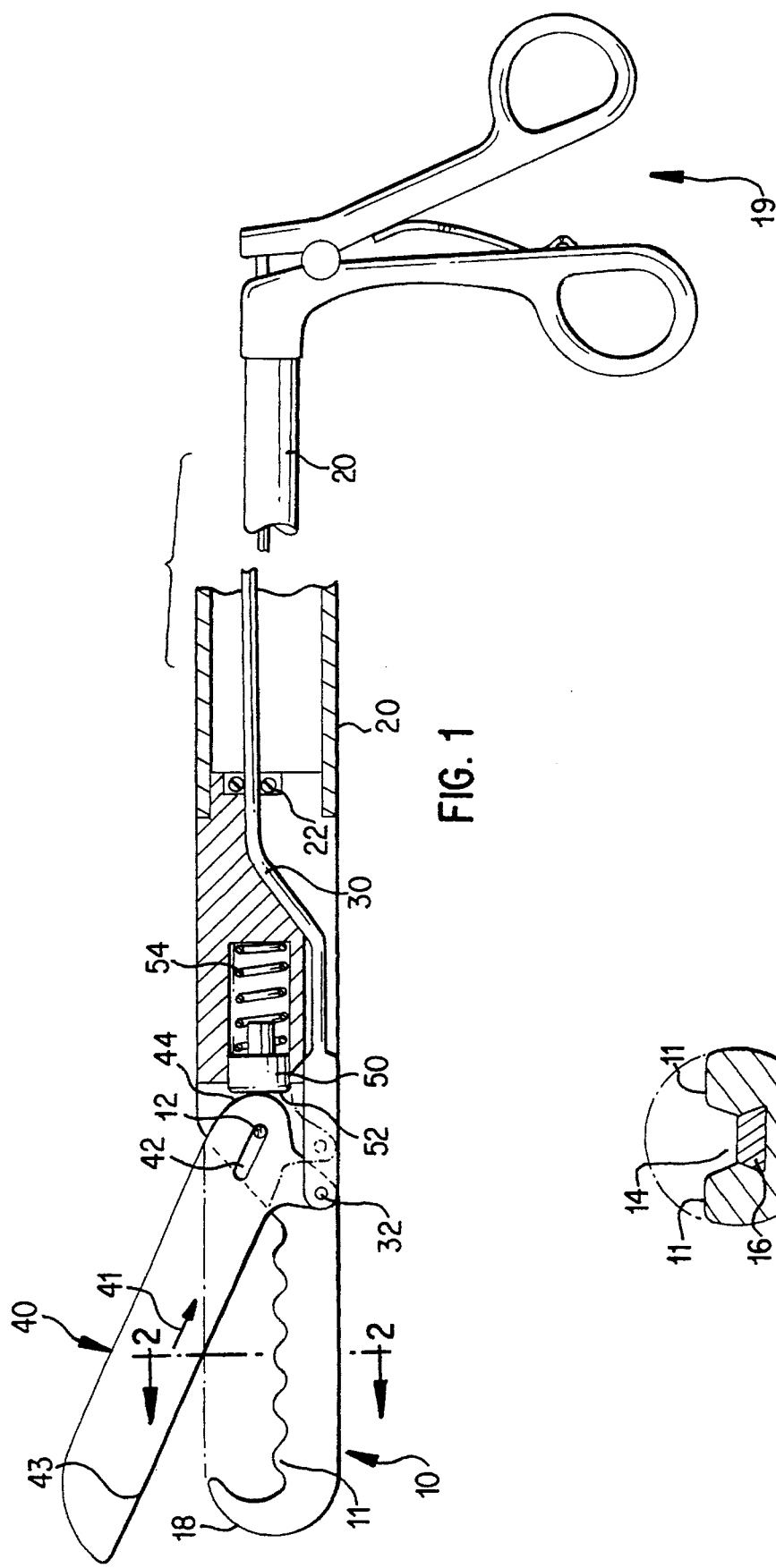

ANVIL SHEARS FOR SURGICAL PURPOSES

BACKGROUND OF THE INVENTION

The invention relates to anvil shears for surgical purposes, particularly for laparoscopic operations, with an anvil fixed to the distal end of an instrument tube and a blade pivotably fitted to the anvil. The blade is pivotable against the anvil by means of an operating rod that is longitudinally displaceable in the instrument tube. Handle parts are provided that move against one another with a closing movement that is transferred by the operating rod to the blade.

In modern minimum invasive surgery the instruments required for the operation are introduced through trocar cannulas into the interior of the body, e.g. into the abdominal cavity and are guided under the control of an also introduced endoscope or using X-ray observation and actuated for the individual operating steps. Such operating techniques are e.g. used in laparoscopic cholecystectomy and apendectomy, as well as in orthopedic surgery, e.g. operations on the knee joint. Use is inter alia made of shears introducible through trocar cannulas for cutting vessels, fibre bundles and tendons. An optimum cutting action is necessary particularly when cutting through hard and fibrous tissue, so that the disection takes place in one cut using a blade closing movement, because several movements on the part of the blade and the instrument can cause traumatization of the surrounding tissue. In addition, the performance of a precise cut under endoscopic conditions is complicated, if the shears have to be closed several times with an obstinate material for cutting. For the surgeon it is a complicated, time-consuming task to fix the shears to the same cutting point a number of times, as a result of the restricted observation conditions, which endoscopically only allow a bidimensional observation of the operating area.

SUMMARY OF THE INVENTION

The problem of the invention is to provide anvil shears for laparoscopic operations, which lead to an improved cutting action.

According to the invention, the blade pivotable against the fixed anvil is displaceably mounted in its longitudinal direction, so that, besides the pivoting movement, there can be a longitudinal, cutting movement of the blade. For this purpose the blade is subject to a pretensioning force, which has at least one component, which presses the blade forwards into the maximum distal advanced position. As the pivoting movement for closing the blade is performed by a force transmitted via an operating rod in the longitudinal direction of the shears, a corresponding force is exerted on the blade bearing and is opposed to the pretensioning force. Thus, the blade is displaced until the force exerted with the operating rod for closing purposes is compensated by the pretensioning force, which increases with increasing displacement path. Thus, on closing the blade, independently of the resistance of the material for cutting between the blade and the anvil, additionally a longitudinal blade movement is caused, so that a blade sawing movement over the material for cutting is performed with an improved cutting action.

According to an advantageous embodiment the blade is fitted to the anvil with a joint bolt fixed to the latter and which is passed through an elongated hole in the blade, which extends in the longitudinal direction thereof. The pretensioning of the blade in the distal advanced position is advantageously brought about in that at the rear a sliding element is applied to the blade and is displaceably guided in the anvil in the shear longitudinal direction and is subject to a spring tension, so that the latter is transferred to the blade. With a rear roundness the blade slideably engages on a bearing surface, which is formed by the front face of the sliding element.

In a further advantageous embodiment the anvil is provided with a corrugation or teeth on either side of the surface of cut. This construction has the advantage that the material for cutting is securely held on the surface of cut and cannot move longitudinally with the blade.

The surface of cut on the anvil against which the blade cutting edge cuts, is advantageously provided with a material insert, which is softer than the blade and is e.g. TEFLON (polyflourethylenpropylen).

The inventive shears are advantageously constructed as hook shears, which have a hook emanating from the distal end of the anvil.

In a further embodiment the anvil and the blade can be supplied by a high frequency current, in order to coagulate vessels in the operating area.

The blade cutting edge can be made from steel or ceramic material. The cutting edge can either be smooth or serrated.

The invention is described in greater detail hereinafter relative to an embodiment and the attached drawings, wherein show:

BRIEF DESCRIPTION OF THE DRAWINGS

FIG. 1 a side view of the front, distal part of inventive anvil shears in a partial section.

FIG. 2 a section through the anvil along line 2 of FIG. 1.

DETAILED DESCRIPTION OF THE DRAWINGS

The shears shown with the distal end in FIG. 1 have an elongated instrument tube 20, to which the anvil 10 is firmly connected. The blade 40 is pivotably held on the anvil 10 with a joint bolt 12. A tie rod 30 is longitudinally displaceably guided in the instrument tube 20 under the control of handle 19 and is passed out of the instrument to be 20 via a packing 22. The blade pivotable about the joint bolt 12 is closed by the tie rod 30, which is fixed to the blade 40 in displaced manner with respect to the pivot pin. The blade 40 and tie rod 30 are coupled with a rotary connection formed by a bolt 32. The tie rod 30 is actuated at the proximal shear end by means of not shown handle members moved against one another. On compressing the handle members a tension is exerted by means of the tie rod 30 on the blade 40, which by its fixture displaced with respect to the pivot pin or axis brings about a torque and closes the blade 40 against the fixed anvil 10.

To permit a longitudinal displacement of the blade 40 in addition to its pivoting, an elongated hole 42 is provided in the blade 40 and through it is passed the joint bolt 12. The elongated hole 42 extends in the longitudinal direction of the blade 40, so that the latter can be moved in the direction of the arrow 41 against the anvil.

As stated, the blade 40 is closed by the tension of the tie rod 30 applied to the blade in displaced manner with respect to the fulcrum. To permit the absorption on the blade 40 of this force directed against the instrument tube 20 in the longitudinal direction of the shears, a further blade mounting support must be provided besides the guide in the elongated hole 42. An abutment surface is formed in this embodiment by a bearing surface 52, which is applied at the rear to a roundness 44 on the blade. The roundness 44 is approximately semicircular with the centre of the circle of curvature at the rear end of the elongated hole 42. The bearing surface 52, on which the roundness 44 slides during the pivoting of the blade, is formed by the front face of a slide element 50. The slide element 50 is displaceably held in the longitudinal direction of the shears in a guide on the anvil 10. The sliding element 50 is subject to spring tension by a spiral spring 54. The spring tension acting in the longitudinal direction of the shears is transferred by means of the sliding element 50 to the blade 40, which is consequently held by a pretension in its maximum distal advanced position.

If during its closing movement the blade strikes a material for cutting, which offers a resistance to the further pivoting movement, the force exerted by the tie rod 30 for closing the blade 40 must be increased. This tension on the blade 40 is opposed to the spring tension on the rear bearing surface 52 of the blade, so that the sliding element is movedcounter to the spring tension and consequently there is a displacement of the blade in its longitudinal direction along its guide in the elongated hole 42. Therefore the force applied to the blade for the rotation thereof is absorbed by an oppositely directed, elastic bearing force, so that as a function of the force necessary for closing the blade the bearing surface resiliently gives way and allows a longitudinal movement of the blade. The bearing surface 52 gives way until the increasing spring tension with increasing displacement compensates the tension on the blade. Therefore the cutting longitudinal movement of the blade increases in proportion to the resistance which the material to be cut opposes to the closing of the blade, i.e. a longitudinal movement with a long travel is performed on a hard, difficultly cuttable material and consequently the cutting action is improved.

If the blade closes against a material to be cut, which offers resistance to the closing movement, the blade moves in the direction of the arrow 41 and performs a cutting and sawing longitudinal movement on the material. Close to the closed position, when the cutting edge of the blade 40 is located immediately above the surface of cut of the anvil 10, the blade 40 can then assume the position indicated by the broken line. If the shears are relieved again and opened, as a result of the spring bias the blade 40 again assumes the advanced position shown in continuous line form.

It is readily apparent that variants with respect to the mounting of the blade are possible. For example, in place of a sliding element 50 and spiral spring 54, it would be possible to have spring elements fixed between the joint bolt 12 and an opposite point on the blade 40 upstream thereof, such as on the opposite end of the elongated hole 42, in order to force the two apart and therefore keep the blade advanced. There can also be guides for the blade on the anvil not in the form of an elongated hole.

In the present embodiment the shears are in the form of hook shears and the anvil 10 is provided at its distal end with a hook 18. The anvil also has a corrugation 11, in order to hold material for cutting resting thereon and fix against a longitudinal displacement on the anvil 10. This ensures that the material for cutting is fixed against the cutting longitudinal movement of the blade 40. The corrugation 11 is provided laterally of the surface of cut of the anvil 10 against which the blade cuts, as can be seen in the sectional representation of FIG. 2. Between the outer corrugations 11 is provided a planar surface of cut 14, which has a material insert 16 in the anvil. A preferred material for the insert 16 is TEFLON (polyflourethylenpropylen). In the same way as the corrugation 11, the hook 18 is constructed in two-part manner on either side of the surface of cut 14, so that the blade 40 can move on the latter undisturbed by the hook 18.

We claim:

1. Anvil shears for surgical purposes, comprising:

an anvil, which is fixed to a distal end of an instrument tube;

a blade pivotably fitted to the anvil and longitudinally displaceable with respect to the anvil;

an operating rod longitudinally displaceable in the instrument tube and coupled to the blade such that movement of the operating rod pivots the blade with respect to the anvil;

handle parts movable against one another and coupled to the operating rod to control longitudinal displacement of the operating rod; and a spring pressing the blade with a spring force towards a distal end of the anvil shears, the spring force having a magnitude that allows the blade to move longitudinally relative to the anvil towards a proximal end of the anvil shears when a closing force exceeds the spring force to thereby provide a sawing cut.

2. Anvil shears for surgical purposes according to claim 1, wherein the blade is fitted to the anvil by a pin fixed to the anvil and which is guided in an elongated hole on the blade, which extends along a longitudinal axis of the blade.

3. Anvil shears for surgical purposes according to claim 1, wherein the blade has a rounded rear surface that slidably engages on a bearing surface on a sliding element, the sliding element being displaceably guided in the anvil in the longitudinal direction of the shears and pretensioned by the spring, so that the blade is biased towards a distal advanced position.

4. Anvil shears for surgical purposes according to claim 1, wherein the anvil has a cutting surface and a corrugation that is lateral of the cutting surface.

5. Anvil shears for surgical purposes according to claim 1, wherein the anvil with an insert made from a material which is softer than the blade material.

6. Anvil shears for surgical purposes according to claim 1, wherein the anvil has a hook such that the anvil shears form hook shears.

7. Anvil shears for surgical purposes according to claim 1, wherein the anvil and blade can be supplied with a high frequency current for coagulating vessels.

8. Anvil shears for surgical purposes according to claim 1, wherein the blade has a cutting edge made from steel.

9. Anvil shears for surgical purposes according to claim 1, wherein the blade has a cutting edge made from ceramic material.

10. Anvil shears for surgical purposes according to claim 1, wherein the blade has a cutting edge with teeth.

* * * * *